United States Patent
Gavini et al.

(10) Patent No.: US 10,105,411 B2
(45) Date of Patent: Oct. 23, 2018

(54) COMPOSITIONS AND METHODS FOR MODULATING AT2R ACTIVITY

(71) Applicant: Novopyxis, Inc., Cambridge, MA (US)

(72) Inventors: Madhavi P. Gavini, Cambridge, MA (US); Raja R. Srinivas, Cambridge, MA (US)

(73) Assignee: Novopyxis Inc., Cambridge, MA (US)

( * ) Notice: Subject to any disclaimer, the term of this patent is extended or adjusted under 35 U.S.C. 154(b) by 0 days.

(21) Appl. No.: 15/595,517

(22) Filed: May 15, 2017

(65) Prior Publication Data

US 2017/0304390 A1 Oct. 26, 2017

Related U.S. Application Data

(63) Continuation of application No. PCT/US2015/061597, filed on Nov. 19, 2015.

(60) Provisional application No. 62/081,839, filed on Nov. 19, 2014.

(51) Int. Cl.
- *A61K 38/08* (2006.01)
- *A61K 48/00* (2006.01)
- *A61K 47/10* (2017.01)
- *A61K 31/7088* (2006.01)

(52) U.S. Cl.
CPC .......... *A61K 38/08* (2013.01); *A61K 31/7088* (2013.01); *A61K 47/10* (2013.01); *A61K 48/005* (2013.01); *A01K 2267/03* (2013.01)

(58) Field of Classification Search
None
See application file for complete search history.

(56) References Cited

U.S. PATENT DOCUMENTS

| | | |
|---|---|---|
| 2003/0130196 A1 | 7/2003 | Rodgers et al. |
| 2004/0123343 A1 | 6/2004 | La Rosa et al. |
| 2009/0094717 A1 | 4/2009 | Troukhan et al. |
| 2012/0035232 A1 | 2/2012 | Steckelings et al. |
| 2012/0157513 A1 | 6/2012 | Li et al. |
| 2013/0333061 A1 | 12/2013 | Wu et al. |

FOREIGN PATENT DOCUMENTS

| | | | |
|---|---|---|---|
| EP | 2455388 A1 | 5/2012 | |
| WO | WO-2006073772 A1 | 7/2006 | |
| WO | WO 2013158628 A1 * | 10/2013 | ........... A61K 31/505 |
| WO | WO-2013158628 A1 | 10/2013 | |
| WO | WO-2016/081733 A2 | 5/2016 | |

OTHER PUBLICATIONS

French et al., "What is a conservative substitution?," J. Mol. Evol. 19:171-175 (1983).*

Yamada et al., "Hypotensive activity of novokinin, a potent analogue of ovokinin(2-7), is mediated by angiotensin AT2 receptor and prostaglandin IP receptor," Peptides 29:412-418 (2008).*

Wang, "Lyophilization and development of solid protein Pharmaceuticals," Int. J. Pharm. 203:1-60 (2000).*

Abadir, P. M., et al., "Identification and Characterization of a Functional Mitochondrial Angiotensin System," Proc. Natl. Acad. Sci. (USA), vol. 108, No. 36, pp. 14849-14854 (Sep. 6, 2011).

Abdalla, S., et al., "Angiotensin II $AT_2$ Receptor Oligomers Mediate G-protein Dysfunction in an Animal Model of Alzheimer Disease," J. Biol. Chem., vol. 284, No. 10, pp. 6554-6565 (Mar. 6, 2009).

Adachi, Y., et al., "Angiotensin II type 2 receptor deficiency exacerbates heart failure and reduces survival after acute myocardial infarction in mice," Circulation, vol. 107, pp. 2406-2408 (2003).

Ali, Q, et al., "Chronic AT2 receptor activation increases renal ACE2 activity, attenuates AT1 receptor function and blood pressure in obese Zucker rats", Kidney International, vol. 84, pp. 931-939, published online Jul. 3, 2013 (9 pages).

Bae, J., et al., "MCL-1S, a splicing variant of the antiapoptotic BCL-2 family member MCL-1, encodes a proapoptotic protein possessing only the BH3 domain," J. Biol. Chem., vol. 275, No. 33, pp. 25255-25261 (Aug. 18, 2000).

Benigni, A., et al., "Disruption of the Ang II Type 1 Receptor Promotes Longevity in Mice," J. Clin. Invest., vol. 119, No. 3, pp. 524-530 (2009).

Borlongan, C. V., et al., "The great migration of bone marrow-derived stem cells toward the ischemic brain: therapeutic implications for stroke and other neurological disorders," Prog. Neurobiol., vol. 95, No. 2, pp. 213-228, Author Manuscript—36 total pages (Oct. 2011).

Bottari et al. (1992), "Characterization and distribution of angiotensin II binding sites in fetal and neonatal astrocytes from different rat brain regions," Brain Res. 585:372-376.

Brown et al. (2006), "AT2 receptor stimulation may halt progression of pheochromocytoma," Ann. N.Y. Acad. Sci. 1073:436-43.

Carey, R. M., et al., "Role of the Angiotensin Type 2 Receptor in the Regulation of Blood Pressure and Renal Function," Hypertension, vol. 35, No. 1, pp. 155-163 (2000).

Chakrabarty, A., et al., "Estrogen Elicits Dorsal Root Ganglion Axon Sprouting via a Renin-Angiotensin System," Endocrinology, vol. 149, No. 7, pp. 3452-3460 (2008).

Deane, E. C., et al., "Enhanced recruitment of endosomal Na+/H+ exchanger NHE6 into Dendritic spines of hippocampal pyramidal neurons during NMDA receptor-dependent long-term potentiation." J. Neurosci., vol. 33, No. 2, pp. 595-610 (Jan. 9, 2013).

Doi, C., et al., "Angiotensin II type 2 receptor signaling significantly attenuates growth of murine pancreatic carcinoma grafts in syngeneic mice," BMC Cancer, vol. 10, No. 67, pp. 1-13 (2010).

(Continued)

Primary Examiner — Julie Ha
Assistant Examiner — Kristina M Hellman
(74) Attorney, Agent, or Firm — Wilmer Cutler Pickering Hale and Dorr LLP

(57) ABSTRACT

New polypeptide agonists of AT2R are disclosed, as well as pharmaceutical compositions comprising the agonists, methods of their use in the treatment of diseases, conditions or disorders characterized by insufficient AT2R activity or excessive AT1R activity, and methods of their use as laboratory reagents for research purposes.

7 Claims, 4 Drawing Sheets

Specification includes a Sequence Listing.

(56) References Cited

OTHER PUBLICATIONS

Dronavalli, S., et al., "The pathogenesis of diabetic nephropathy," Nat. Clin. Pract. Endocrinol. Metab., vol. 4, No. 8, pp. 444-452 (Aug. 2008).
Ferreira, A. J., et al., "Therapeutic implications of the vasoprotective axis of the renin-angiotensin system in cardiovascular diseases," Hypertension, vol. 55, No. 2, pp. 207-213 (2010).
Gendron et al. (2003), "The angiotensin type 2 receptor of angiotensin II and neuronal differentiation: from observations to mechanisms," J. Mol. Endocrinol. <http://www.ncbi.nlm.nih.gov/pubmed/14664700> 31(3):359-72.
Guimond and Gallo-Payet (2012), "How does angiotensin AT(2) receptor activation help neuronal differentiation and improve neuronal pathological situations?" Front Endocrinol. (Lausanne) 3:164. (12 pages).
Guimond et al. (2013), "Expression and role of the angiotensin II AT2 receptor in human prostate tissue: in search of a new therapeutic option for prostate cancer." The Prostate 73(10):1057-1068.
Guimond, MO et al., "The Angiotensin II Type 2 Receptor in Brain Functions: An Update", International Journal of Hypertension, Article ID 351758, vol. 2012 (19 pages).
Gul et al. (2012), "RAS-Mediated Adaptive Mechanisms in Cardiovascular Tissues: Confounding Factors of RAS Blockade Therapy and Alternative Approaches," Cardiorenal Med. 2(4):268-280.
Harel et al. (2012), "The Effect of Combination Treatment with Aliskiren and Blockers of the Renin-angiotensin System on Hyperkalaemia and Acute Kidney Injury: Systematic Review and Meta-analysis." BMJ 344(1) (13 pages).
Herr et al. (2008), "Potential role of Renin-Angiotensin-system for tumor angiogenesis in receptor negative breast cancer," Gynecol. Oncol. 109:418-25.
Hetrick et al. (2008), "Ligand mediated protein-protein interaction between the angiotensin receptor type AT1 and the human NHE6 isoform." FASEB J. 22:726.5. (abstract only) (2 pages).
Hook et al. (2005), "The Proteolytic Stability of 'Designed' Beta-peptides Containing Alpha-peptide-bond Mimics and of Mixed Alpha,beta-peptides: Application to the Construction of MHC-binding Peptides," Chem. Biodivers. 2(5):591-632.
Yayama et al. (2006), "Angiotensin II stimulates endothelial NO synthase phosphorylation in thoracic aorta of mice with abdominal aortic banding via type-2 receptor," Hypertension 48:958-964.
Iwanami et al. (2011), "Effect of angiotensin II type 2 receptor deletion in hematopoietic cells on brain ischemia-reperfusion injury," Hypertension 58(3):404-409.
Kalupahana and Moustaid-Moussa, "The renin-angiotensin system: a link between obesity, inflammation and insulin resistance," (2012) Obes. Rev. 13(2):136-49.
Kintscher et al. (2009), "Inhibiting angiotensin type 1 receptors as a target for diabetes," Expert Opin. Ther. Targets 12:1257-63.
Knowle et al. (2000), "Identification of an interaction between the angiotensin II receptor sub-type AT2 and the ErbB3 receptor, a member of the epidermal growth factor receptor family," Regul. Pept. 87(1-3):73-82.
Kumar et al. (2002), "Identification of the Region of AT2 Receptor Needed for Inhibition of the AT1 Receptor-mediated Inositol 1,4,5-triphosphate Generation." FEBS Lett. 532(3):379-86.
Kurihara et al. (2006), "Neuroprotective Effects of Angiotensin II Type 1 Receptor (AT1R) Blocker, Telmisartan, via Modulating AT1R and AT2R Signaling in Retinal Inflammation," Invest. Ophthalmol. Vis. Sci. 47(12):5545-5552.
LaMarca (2011), "Hypertension in Response to IL-6 During Pregnancy: Role of AT1-receptor Activation." Int. J. Interferon Cytokine Mediator Res. 2011(3):65-70.
Lehtonen et al. (1999), "Analysis of functional domains of angiotensin II type 2 receptor involved in apoptosis," Mol. Endocrinol. 13(7):1051-60.
Lenkei et al. (1996), "Distribution of angiotensin II type-2 receptor (AT2) mRNA expression in the adult rat brain," J. Comp. Neurol. 373:322-339.
Lenkei et al. (1997), "Expression of angiotensin type-1 (AT1) and type-2 (AT2) receptor mRNAs in the adult rat brain: a functional neuroanatomical review," Front. Neuroendocrinol. 18:383-439.
Libby et al. (2002), "Inflammation and Atherosclerosis," Circulation 105(9):1135-1143.
Liebson and Amsterdam (2009), "Ongoing Telmisartan Alone and in Combination With Ramipril Global Endpoint Trial (ONTARGET): Implications for Reduced Cardiovascular Risk." Prev. Cardiol. 12(1):43-50.
McCarthy et al. (2009), "Angiotensin AT2 receptor stimulation causes neuroprotection in a conscious rat model of stroke," Stroke 40:1482-9.
Mendelsohn et al. (1988), "Localization of angiotensin II receptor binding in rabbit brain by in vitro autoradiography," J. Comp. Neurol. 270:372-384.
Mitra et al. (2010), "Angiotensin II-induced Upregulation of AT1-receptor Expression: Sequential Activation of NFkB and Elk-1 in Neurons." Am. J. Physiol. Cell Physiol. 299(3):C561-9.
Mizushima et al. (2010), "Blockage of Angiotensin II Type 1 Receptor Regulates TNF-$\alpha$-induced MAdCAM-1 Expression via inhibition of NF-$\kappa$B translocation to the nucleus and ameliorates colitis." Am. J. Physiol. Gastrointest. Liver Physiol. 298(2):G255-G266.
Nahmod et al. (2003), "Control of dendritic cell differentiation by angiotensin II," FASEB J. 17(3):491-493 (19 pages).
Namsolleck et al., "AT2-receptor stimulation enhances axonal plasticity after spinal cord injury by upregulating BDNF expression," Neurobiol Dis. 51:177-91.
Nuyt et al. (1999), "Ontogeny of angiotensin II type 2 receptor mRNA expression in fetal and neonatal rat brain," J. Comp. Neurol. 407:193-206 (14 pages).
Ohinata et al. (2009), "Orally administered novokinin, an angiotensin AT2 receptor agonist, suppresses food intake via prostaglandin E2-dependent mechanism in mice," Peptides 30:1105-1108.
Oishi et al. (2006), AT2 receptor mediates the cardioprotective effects of AT1 receptor antagonist in post-myocardial infarction remodeling, Life Sci. 80(1):82-8.
Okamura et al. (1999), "Upregulation of renin-angiotensin system during differentiation of monocytes to macrophages," J. Hypertens. 17(4):537-545.
Padia et al. (2012), "Mechanisms of dopamine D(1) and angiotensin type 2 receptor interaction in natriuresis," Hypertension 59(2):437-45.
Parving et al. (2012), "Cardiorenal End Points in a Trial of Aliskiren for Type 2 Diabetes." New Eng. J. Med. 367(23):2204-2213.
Phillips (1987), "Functions of angiotensin in the central nervous system," Ann. Rev. Physiol. 49:413-435.
Pickel et al. (2010), "Overexpression of angiotensin II type 2 receptor gene induces cell death in lung adenocarcinoma cells," Cancer Biol. Ther. 9(4):277-85.
Pulakat et al. (2002), "Role of C-terminal cytoplasmic domain of the AT2 receptor in ligand binding and signaling," FEBS Lett. 524(1-3):73-8.
Pulakat et al. (2005), "Ligand-dependent complex formation between the Angiotensin II receptor subtype AT2 and Na+/H+ exchanger NHE6 in mammalian cells," Peptides 26(5):863-73.
Pulakat et al. (2005), "Roles of the intracellular regions of angiotensin II receptor AT2 in mediating reduction of intracellular cGMP levels," Cell Signal. 17(3):395-404.
Qi et al. (2012), "Moderate cardiac-selective overexpression of angiotensin II type 2 receptor protects cardiac functions from ischemic injury," Exp. Physiol. 97:89-101.
Grammatopoulos, et al. (2005), "Angiotensin II protects cultured midbrain dopaminergic neurons against rotenone-induced cell death," Brain Res. 1045(1-2):64-71.
Rodrigues-Ferreira and Nahmias (2010), "An ATIPical family of angiotensin II AT2 receptor-interacting proteins," Trends Endocrinol. Metab. 21:684-690.
Rodriguez-Pallares et al. (2004), "Angiotensin II increases differentiation of dopaminergic neurons from mesencephalic precursors via angiotensin type 2 receptors," *Eur. J. Neurosci.* 20(6):1489-98.

(56) References Cited

OTHER PUBLICATIONS

Saavedra et al. (2011), "Blockade of brain angiotensin II AT1 receptors ameliorates stress, anxiety, brain inflammation and ischemia: Therapeutic implications," Psychoneuroendocrinology 36(1):1-18.
Salomone, L. J. et al., (2007) "Intrarenal Dopamine D1-Like Receptor Stimulation Induces Natriuresis via an Angiotensin Type-2 Receptor Mechanism", Hypertension, 49:155-161, originally published online Nov. 20, 2006 (8 pages).
Santos et al., "The Therapeutic Role of Renin-Angiotensin System Blockers in Obesity-Related Renal Disorders," (2014) Curr. Clin. Pharmacol. 9(1):2-9.
Schnapf, J. L., "Visual Transduction in Cones of the Monkey *Macaca fascicularis*," Journal of Physiology, vol. 427, pp. 681-713 (1990).
Schwede et al. (2013), "Genes for Endosomal NHE6 and NHE9 Are Misregulated in Autism Brains," Mol. Psychiatry 19(3):277-9.
Severs and Daniels-Severs (1973), "Effects of angiotensin on the central nervous system," Pharmacol. Rev. 25:415-449.
Shieh et al. (2009), "Modification of alternative splicing of Mcl-1 pre-mRNA using antisense morpholino oligonucleotides induces apoptosis in basal cell carcinoma cells," J. Invest. Dermatol. 129(10):2497-506.
Siragy and Carey (1997), The subtype 2 (AT2) angiotensin receptor mediates renal production of nitric oxide in conscious rats, J. Clin. Invest. 100:264-269.
Smith, M. T., et al., "A Small Molecule Angiotensin II Type 2 Receptor (AT2R) Antagonist Produces Analgesia in a Rat Model of Neuropathic Pain by Inhibition of p38 Mitogen-Activated Protein Kinase (MAPK) and p44/p42 MAPK Activation in the Dorsal Root Ganglia," Pain Medicine, vol. 14, No. 10, pp. 1557-1568 (Oct. 1, 2013).
Song et al. (1992), "Mapping of angiotensin II receptor subtype heterogeneity in rat brain," J. Comp. Neurol. 316:467-484.
Steckelings et al. (2012), "AT2 receptor agonists: hypertension and beyond," Curr. Opin. Nephrol. Hypertens. 21(2):142-6.
Thathiah and De Strooper (2011), "The Role of G Protein-coupled Receptors in the Pathology of Alzheimer's Disease," Nat. Rev. Neurosci. 12(2):73-87.
Thomas et al. (2010), "Mcl-1: the molecular regulation of protein function," FEBS Lett. 584(14):2981-9.
Unger (2003), "The Ongoing Telmisartan Alone and in Combination with Ramipril Global Endpoint Trial Program," Am. J. Cardiol. 91(10A):28G-34G.
Unger and Dahlöf (2010), "Compound 21, the first orally active, selective agonist of the angiotensin II type 2 (AT2) receptor: implications for AT2 receptor research and therapeutic potential," J. Renin Angiotensin Aldosterone Syst. 11:75-7.
Unger et al. (1988), "Brain angiotensin: pathways and pharmacology," Circulation 77(60):I40-54.
Vinson et al. (2012), "The renin-angiotensin system in the breast and breast cancer," Endocr. Relat. Cancer 19(1):R1-19.
von Heijne, "Signal Sequences. The Limits of Variation," Journal of Molecular Biology, 184 (1), 1985, pp. 99-105.
Weir et al. (2012), "CNS SIRT3 Expression Is Altered by Reactive Oxygen Species and in Alzheimer's Disease," PLoS ONE 7(11):e48225.
Widdop et al. (2002), "AT2 receptor-mediated relaxation is preserved after long-term AT1 receptor blockade," Hypertension 40:516-520.
Wruck et al. (2005), "Regulation of transport of the angiotensin AT2 receptor by a novel membrane-associated Golgi protein," Arterioscler. Thromb. Vasc. Biol. 25(1):57-64.
Xinhan et al. (2011), "Na+/H+ Exchanger Isoform 6 (NHE6/SLC9A6) Is Involved in Clathrin-dependent Endocytosis of Transferrin," Am. J. Physiol. Cell Physiol. 301(6):C1431-C1444.
Yamada et al. (1996), "Angiotensin II type 2 receptor mediates programmed cell death," Proc. Natl. Acad. Sci. (USA) 93(1):156-60.
Yang et al. (1996), "MCL-1, a member of the BLC-2 family, is induced rapidly in response to signals for cell differentiation or death, but not to signals for cell proliferation," J. Cell Physiol. 166(3):523-36.
Yang, et al., "Selective Cytotoxicity Following Arg-to-Lys Substitution in Tritrpticin Adopting a Unique Amphipathic Turn Structure," FEBS Letters 540 (2003) pp. 229-233 (5 sheets).
Sokalingam, et al., "A Study on the Effect of Surface Lysine to Arginine Mutagenesis on Protein Stability and Structure Using Green Fluorescent Protein," PLoS ONE, vol. 7, Issue 7, e40410, Jul. 9, 2012, (12 pages).
Yuan, et al., "MYST Protein Acetyltransferase Activity Requires Active Site Lysine Autoacetylation," The EMBO Journal, 31, (Oct. 21, 2011), pp. 58-70 (13 sheets).
Vacca, et al., "Active-site Arg → Lys Substitutions Alter Reaction and Substrate Specificity of Aspartate Aminotransferase," The Journal of Biologicial Chemistry, vol. 272, No. 35, Issue of Aug. 29, 1997, pp. 21932-21937, (7 pages).
Pulakat, et al., "Role of Lys215 Located in the Fifth Transmembrane Domain of the AT2 Receptor in Ligand-Receptor Interaction," Regulatory Peptides, 73, (1998) pp. 51-57 (7 sheets).
Louis, et al., "Substitution Mutations of the Highly Conserved Arginine 87 of HIV-1 Protease Result in Loss of Proteolytic Activity," Biochemical and Biophysical Research Communications, vol. 164, Issue 1, 1989, pp. 30-38 (abstract only) (1 sheet).
Yamada et al., "A Potent Hypotensive Peptide, Novokinin, Induces Relaxation by $AT_2$-and IP-Receptor-Dependent Mechanism in the Mesenteric Artery from SHRs," Bioscience, Biotechnology, and Biochemistry, Jan. 7, 2008, 72:1, pp. 257-259 (3 pages).
Steckelings, et al., "The Past, Present and Future of Angiotensin II Type 2 Receptor Stimulation," Journal of the Renin-Angiotensin-Aldosterone System, Mar. 2010, 11:1, pp. 67-73 (7 pages).
Steckelings, et al., "Non-Peptide AT2-Receptor Agonists," Current Opinion in Pharmacology, Apr. 1, 2011, 11, pp. 187-192 (6 pages).
Partial Supplementary European Search Report dated May 25, 2018 received in related European Patent Application No. 15860292.0, 15 pages.

\* cited by examiner

COMPOSITIONS AND METHODS FOR MODULATING AT2R ACTIVITY

CROSS-REFERENCE TO RELATED APPLICATIONS

This application is a continuation of PCT/US15/061597, entitled "Compositions and Methods for Modulating AT2R Activity", and filed on Nov. 19, 2015, which claims priority to U.S. Provisional application 62/081,839, entitled "Compositions and Methods for Modulating AT2R Activity", and filed on Nov. 19, 2014, both of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jan. 19, 2016, is named 220935200122WO1_SL.txt and is 6,228 bytes in size.

FIELD OF THE INVENTION

The invention relates to the fields of molecular biology and biochemistry, and in particular to the development of pharmaceuticals for the modulation of the activity of the Angiotensin II Type 2 Receptor (AT2R).

BACKGROUND

The Angiotensin II Type 2 Receptor AT2R is a member of the anti-inflammatory/vasodilative branch of the renin-angiotensin system (RAS). AT2R-activation ameliorates cardiovascular diseases and stroke, attenuates cancers and exerts a neuroprotective role (1-17).

AT2R is a transmembrane receptor protein comprising a sequence of 363 amino acids which form seven-transmembrane domains. The three-dimensional structure of AT2R has not yet been resolved, but it contains five potential glycosylation sites and a conserved lysine residue (Lys 199 or K199) that is critical for ligand-protein interaction. AT2R also contains a potential protein kinase C phosphorylation site in the second intracellular loop (18).

AT2R belongs to the G-Protein Coupled Receptor (GPCR) family of proteins. AT2R activation stimulates various protein phosphatases (e.g., SHP1, MKP1 and PP2A) and inhibits cancer cell growth. AT2R-mediated activation of the bradykinin/nitric oxide/cGMP pathway and the prostaglandin I2-IP receptor pathway contribute to its vasodilatory effects (19-23). However, many of the signaling mechanisms activated by the AT2R are G-protein independent and involve direct interactions between AT2R and other cellular proteins. AT2R interacts with a family of AT2R-interacting proteins (ATIPs) involved in neuronal differentiation, vascular remodeling and tumor suppression via its C-terminal cytoplasmic domain (CCD) (24). It has been shown that the AT2R interacts with the ErbB family receptors and $Na^+/H^+$ exchanger NHE6 via its third intracellular loop (ICL) and the CCD, and that the third ICL of the AT2R is involved in attenuating Angiotensin II Type 1 Receptor (AT1R) signaling (25, 26). AT2R-mediated apoptosis also requires the third ICL (27, 28). Interestingly, deletion of the CCD reduces affinity of AT2R to Angiotensin II (Ang II), but increases its affinity to the peptide ligand CGP42112A and enhances Ang II-induced cGMP reduction (29, 30). These observations highlight the roles of the third ICL and the CCD in AT2R signaling.

AT2R down-regulation is seen in Parkinson's Disease (PD) (31). Although not much is known about the role of AT2R in PD, it is known that AT2R activation causes differentiation of dopaminergic neurons from mesencephalic precursors (32). Additionally, AT2R activation is neuroprotective to cultured mid-brain dopaminergic neurons, whereas use of an AT2R antagonist eliminates the neuroprotective effects (33).

Early studies from Mendelsohn et al. (1988) and Unger et al. (1988) established, using biochemical and pharmacological approaches, the existence of a renin-angiotensin system in the brain (34, 35). The various components (e.g., angiotensin-converting enzyme (ACE), Ang II and Ang II receptors) are found in areas of the brain involved in the regulation of fluid and electrolyte balance and in the regulation of arterial pressure (36, 37), as well as in structures involved in cognition, behavior and locomotion. Interestingly, all of these components, and in particular AT2R, are highly expressed during fetal life. This suggests that they could play important roles during development. As reported by Nuyt et al. based on studies conducted in fetal and neonatal rats, AT2R mRNA appeared early (e.g., as early as embryonic day 13) in the differentiating lateral hypothalamic area, but transiently in various developing/differentiating brain structures (38). In most areas, the ontogeny of AT2R mRNA expression is highly correlated with the maturation and differentiation of the different areas themselves (as in the cerebellum, inferior olivary complex, and medullary motor nuclei innervating the tongue, perioral, and jaw muscles, where AT2R expression dramatically diminished in the mature neurons).

From studies conducted in cell lines, it appears that activation of AT2R during development is involved in neurite elongation, neuron migration, neuronal death and survival balance, as well as in the establishment and maintenance of synaptic connections. In the adult rat, AT2R was found at high levels in the medulla oblongata (which controls autonomous functions), in septum and amygdala (which are associated with anxiety-like behavior), in the thalamus (which is associated with sensory perception), in the superior colliculus (which controls eye movements in response to visual information and is linked to blink hyperexcitability in Parkinson's), as well as in the subthalamic nucleus and in the cerebellum (areas associated with learning of motor functions) (39, 40, 41).

According to Bottari et al., AT2Rs are found on neurons, but not on astrocytes or glial cells. The presence of AT2R in restricted brain areas of the adult and its wide distribution in the fetus (in many differentiating structures and nuclei) are indicative of a role in neuronal function and neuronal development respectively (42). Accordingly, using cells of neuronal origin and models of neuronal regeneration, AT2R was found to be involved in the regulation of apoptosis and cell differentiation. Apart from its transient expression in many structures during development, expression of AT2R increases in the brain after cellular damage, which shows that it plays a role in neuronal wound healing. In addition to neuronal differentiation, which is of paramount importance in nerve regeneration, AT2R also stimulates differentiation of hematopoietic cells, a key process during regeneration and reconstruction (31).

Ischemic damage is characterized by infiltration of a number of hematopoietic cells such as platelets, macrophages, and leukocytes (43). Significantly, AT2R has the capacity to induce differentiation of human monocytes into dendritic cells (44), indicating a potential protective effect. Confirming this protective effect of AT2R is the observation that ischemic damage was found to be greater in mice with hematopoietic cells deleted in AT2R expression (45). These findings show that expression and activation of AT2R in hematopoietic cells is part of its beneficial effect following brain injury (46).

Renal dopamine $D_1$-like receptors ($D_1$Rs) and AT2Rs are important natriuretic receptors counter-balancing AT1R-mediated tubular sodium reabsorption. In uninephrectomized, sodium-loaded Sprague-Dawley rats, direct renal interstitial infusion of the highly selective $D_1$R agonist fenoldopam induced a natriuretic response that was abolished by the AT2R-specific antagonist PD-123319 or by the microtubule polymerization inhibitor nocodazole but not by the actin polymerization inhibitor cytochalasin D. The results demonstrate that $D_1$R-induced natriuresis requires AT2R recruitment to the apical plasma membranes of renal proximal tubule cells in a microtubule-dependent manner involving an adenylyl cyclase/cAMP signaling pathway. These studies provide novel insights regarding the mechanisms whereby renal $D_1$Rs and AT2Rs act in concert to promote sodium excretion in vivo (47).

Treatments of primary neurons with Compound 21 (C21), an AT2R agonist, improved functional recovery in experimental spinal cord injury through promotion of axonal plasticity and through neuroprotective and anti-apoptotic mechanisms (48).

Even though AT2R belongs to the GPCR family of proteins, its signaling mechanisms are atypical and remain elusive. Activated AT2R induces a vasodilator cascade of bradykinin (BK)/Nitric Oxide/cGMP, stimulates various protein phosphatases (e.g., SHP1, MKP1 and PP2A) and inhibits cancer cell growth (19-23). AT2R also interacts with a family of AT2 receptor interacting proteins (ATIPs) involved in neuronal differentiation, vascular remodeling and tumor suppression via its CCD (49, 50). Chronic AT1 Receptor blocker (ARB) treatment can result in redirecting Ang II to AT2R that is usually co-expressed with AT1R in cardiovascular tissues, leading to increased AT2R activation, and enhanced AT1R-AT2R cross-talk. In AT2R knock-out mice, ARBs failed to attenuate acute-phase post-infarction remodeling indicating that AT2R is required for the cardioprotective effects of ARBs (17).

Cardiovascular protective effects of AT2R are highlighted by the fact that moderate cardiac-specific AT2R overexpression protects the heart from ischemic injury (16).

The inflammatory cascade contributing to the development of cardiovascular disease (CVD) has been rapidly elucidated over the past decade, inspired by the marked increase in disease prevalence. To put this in perspective, nearly 70% of all Type 1 Diabetes Mellitus (T1DM) fatalities are attributed to the condition (51). Increased activation of the pro-inflammatory AT1R is seen in cardiovascular disease and hypertension (3). In general, increased AT1R activation up-regulates pro-inflammatory and pro-cancerous proteins such as nf-kb, IL-6 (52, 53, 54).

Diabetic nephropathy is marked by increased basal levels of certain cytokines (e.g., TNF-alpha, IL-6) and therefore experimental treatments have focused on modulating these same markers. Multiple studies have revealed that levels of cytokines in serum and urine are positively correlated with the progression of the disease. Particularly related to the pathogenesis of nephropathy, molecules such as IL-6 have been identified as being responsible for altering the permeability of vascular endothelial cells and the development of basement membrane thickening, respectively (55).

Chronic activation of RAS systemically and locally elevates Ang II. Ang II then binds to AT1R and induces signaling pathways that promote muscle constriction, salt and water retention, fibrosis, hypertrophy and hyperplasia that underlie many of the metabolic diseases and poor cardiovascular and renal prognosis. Blockade of RAS can be exerted at multiple levels: via inhibition of Renin, ACE, or AT1R signaling (1, 2, 5, 9). Efficient RAS blockers at all these levels have been developed and are currently in use to block over-activation of RAS and to offer protection from RAS-related metabolic diseases including diabetes (2).

However, evidence from randomized clinical trials such as the Aliskiren Trial in Type 2 Diabetes Using Cardio-Renal Endpoints (ALTITUDE) and the Ongoing Telmisartan Alone and in Combination With Ramipril Global Endpoint Trial (ONTARGET) shows that dual RAS blockade was not beneficial compared to monotherapy in preventing serious outcomes in patients with known vascular disease or diabetes with end-organ damage (56-58). Clinical evidence supporting the association of RAS inactivation to renal diseases and basic research on RAS have begun to unveil the intricate self-regulatory signaling loops that fine-tune RAS activation and the adaptive/protective role of RAS in many tissues (9). In this context, Ang II manifests its vasodilative/cardiovascular protective/anti-inflammatory effects when it activates AT2R.

Mitochondria also express a local angiotensin system (MAS). Importantly, AT2R located in the inner membrane of mitochondria plays a significant role in mediating mitochondrial respiration. It is known that during the aging process, mitochondrial AT2R expression is reduced, while the expression of the pro-inflammatory AT1R is increased (62). The critical role of MAS in aging indicates that this system plays a role in Alzheimer's Disease (AD) development. In further support, it has been shown that amyloid-beta leads to the increased oligomerization and loss of function of the AT2R receptor, which is thought to contribute to pathogenesis of the disease (63,64).

AT1R blockers (ARBs) have been reported to reduce age related mitochondrial dysfunction, attenuate hypertension-induced renal mitochondrial dysfunction, and protect against cardiac mitochondrial dysfunction in the setting of acute ischemia (62,65). Inhibition of AT1R by ARBs theoretically allows more Ang II to bind and activate AT2R. Therefore, elevation of the opposing AT2R system will provide additional improvements in mitochondrial function. Disruption of AT1R was associated with an increased number of mitochondria and up-regulation of the prosurvival genes nicotinamide phosphoribosyltransferase (Nampt) and sirtuin 3 (Sirt3) in the kidney, leading to marked prolongation of life span in mice (66). Of these genes, Sirt3 is known to regulate AD-mediated stress (67).

NHE6 is a mitochondrial protein located in the inner membrane of mitochondria known to improve cognition and memory, and mutations in the NHE6 gene are linked with various neurological disorders such as autism and Christianson's Syndrome (68-70). It has been shown that AT2R interacts with NHE6 via its third ICL. AT2R inhibits AT1R-mediated threonine/tyrosine phosphorylation of NHE6 (71-73). This indicates that AT1R-mediated phosphorylation is a tag for degradation that is prevented via the AT2R-NHE6 interaction.

MCL-1 (myeloid leukemia cell differentiation protein) is a protein that is a member of the Bcl-2 family (74). There are two distinct variants of MCL-1, based on alternative splicing: a long form and two shorter isoforms. The long form (MCL-1L) contains 312 residues, while the short isoforms (MCL-1S) is 271 residues, with the 41 residue difference occurring at the C terminus. MCL-1L contains the standard domains found in the Bcl-2 family including BH1, BH2, BH3, and a transmembrane domain. In contrast, MCL-1S only contains the BH3 domain. This alternative splicing leads to two vastly different biological functions for MCL-1L and MCL-1S. Specifically, MCL-1L is known to be anti-apoptotic while the MCL-1S in complete contrast is pro-apoptotic (75,76). The BH3-like domain region of MCL-1S can bind and dimerize with MCL-1L (77). This interaction inhibits MCL-1 biological activity and therefore MCL-1S is an antagonist to MCL-1L.

SUMMARY OF THE INVENTION

The present invention is based, at least in part, upon the identification of a class of specific small agonists which bind to the Angiotensin 2 Type II Receptor (AT2R), thereby activating the receptor. The agonists are useful as research, diagnostic and therapeutic reagents, particularly in methods for research, diagnosis and treatment relating to diseases, conditions or disorders characterized by insufficient AT2R activity or excessive AT1R activity. The AT2R agonists of the invention are polypeptides (or polypeptide derivatives or analogues) comprising 6 amino acid residues with the generic sequence A1-A2-A3-A4-A5-A6, where A1 is Lys; A2 is Pro, 3Hyp or 4Hyp; A3 is Leu or Ile; A4 is Lys, A5 is Pro, 3Hyp or 4Hyp, and A6 is Trp (SEQ ID NO. 1). Thus, the AT2R. agonists of the invention include polypeptides (or polypeptide derivatives or analogues) comprising, consisting of, or consisting essentially of any of the sequences: Lys-Pro-Leu-Lys-Pro-Trp (SEQ ID NO. 2); Lys-3Hyp-Leu-Lys-Pro-Trp (SEQ ID NO. 3); Lys-4Hyp-Leu-Lys-Pro-Trp (SEQ ID NO. 4); Lys-Pro-Ile-Lys-Pro-Trp (SEQ ID NO. 5); Lys-3Hyp-Ile-Lys-Pro-Trp (SEQ ID NO. 6); Lys-4Hyp-Ile-Lys-Pro-Trp (SEQ ID NO. 7); Lys-Pro-Leu-Lys-3Hyp-Trp (SEQ ID NO. 8); Lys-3Hyp-Leu-Lys-3Hyp-Trp (SEQ ID NO. 9); Lys-4Hyp-Leu-Lys-3Hyp-Trp (SEQ ID NO. 10); Lys-Pro-Ile-Lys-3Hyp-Trp (SEQ ID NO. 11); Lys-3Hyp-Ile-Lys-3Hyp-Trp (SEQ ID NO. 12); Lys-4Hyp-Ile-Lys-3Hyp-Trp (SEQ ID NO. 13); Lys-Pro-Leu-Lys-4Hyp-Trp (SEQ ID NO. 14); Lys-3Hyp-Leu-Lys-4Hyp-Trp (SEQ ID NO. 15); Lys-4Hyp-Leu-Lys-4Hyp-Trp (SEQ ID NO. 16); Lys-Pro-Ile-Lys-4Hyp-Trp (SEQ ID NO. 17); Lys-3Hyp-Ile-Lys-4Hyp-Trp (SEQ ID NO. 18); and Lys-4Hyp-Ile-Lys-4Hyp-Trp (SEQ ID NO. 19). In some embodiments, when A2 is Pro, A5 is 3Hyp or 4 Hyp. In some embodiments, when A5 is Pro, A2 is 3Hyp or 4-Hyp.

Thus, in one aspect, the invention provides AT2R agonist compositions, including reagent grade and pharmaceutical compositions comprising an AT2R agonist, optionally in lyophilized form or in combination with a pharmaceutically acceptable carrier.

In another aspect, the invention provides methods for activation of AT2R in a mammalian cell in vitro using an AT2R agonist composition of the invention. In some embodiments, the method is used to as a control to characterize and/or quantify downstream effects of receptor activation (e.g., effects on mammalian target of rapamycin (MTOR), NHE6, ErbB3, Nitric Oxide Synthase activity, MCL-1 and prostaglandin 12-IP). The AT2R agonist reagent compositions can also be used in vivo as a control for, or competitive or non-competitive inhibitor of, activation of AT2R or inactivation of AT1R in response to treatments with other compounds or drug candidates.

In another aspect, the invention provides methods for the treatment of a subject diagnosed with, at risk of, or otherwise in need of treatment for any diseases, conditions or disorders characterized by insufficient AT2R activity or excessive AT1R activity. The methods involve the administration of a therapeutically effect amount of the AT2R agonist of the invention in a pharmaceutically acceptable carrier to a patient in need thereof. Similarly, the invention provides the AT2R agonists of the invention for use in the preparation or manufacture of a medicament for the treatment of a subject diagnosed with, at risk of, or otherwise in need of treatment for any diseases, conditions or disorders characterized by insufficient AT2R activity or excessive AT1R activity, or insufficient activity of pathways which are downstream of AT2R signaling (e.g., diseases, conditions or disorders characterized by insufficient MTOR, NHE6, ErbB3, Nitric Oxide Synthase, MCL-1 or prostaglandin 12-IP activity or production). Diseases, conditions or disorders suitable for treatment by the methods and with the medicaments of the invention include, without limitation, (a) chronic inflammation caused by over-activation of the AT1R or under-activation of the AT2R; (b) diseases, conditions or disorders for which increasing the circulating levels of at least one MCL-1 isoform is indicated, (c) AT1R-mediated hypertension, (d) AT2R-mediated hypertension and/or cardiovascular disease, (e) AT2R-mediated neurodegenerative disorders, including but not limited to Alzheimer's Disease, Parkinson's Disease, ALS, and age-related mental deterioration, (f) neural injuries (e.g., spinal cord injuries, stroke, ischemia reperfusion injury), (g) cancers, (h) pre-eclampsia, (i) diabetes complications (e.g., retinopathy, pancreatic cell death, metabolic syndrome), (j) inflammation-mediated nephropathy, (k) inflammation-mediated liver disease (e.g., liver cancer, liver failure), (l) inflammation-mediated cardiovascular disease (e.g., myocardial ischemia and injury, myocardial fibrosis, heart attack), (m) pancreatitis, (n) insufficient muscle mass (e.g., muscle wasting due to illness or cancer treatments) (o) AT1R-mediated NHE6 degradation, (p) insufficient mitochondrial activity, and (q) diseases, conditions or disorders characterized by insufficient MTOR, NHE6, ErbB3, Nitric Oxide Synthase, MCL-1 or prostaglandin 12-IP activity or production.

BRIEF DESCRIPTION OF THE DRAWINGS

The following drawings are illustrative of embodiments of the invention and are not meant to limit the scope of the invention as encompassed by the claims.

DETAILED DESCRIPTION

Figures 1A, 1B:
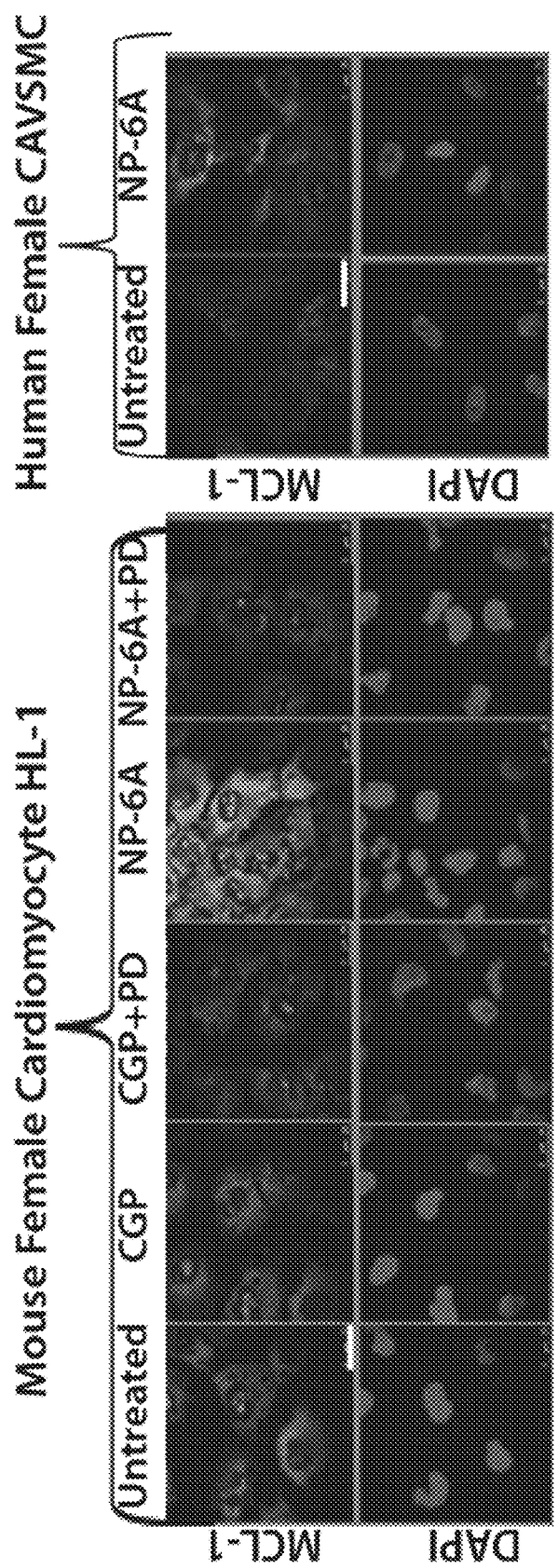
FIGS. 1A and 1B show that an NP-6AK agonist increases MCL-1 expression in female mouse HL-1 cardiomyocytes (FIG. 1A) and human CAVSMCs (FIG. 1B). CGP, a partial agonist was unable to increase MCL-1. Addition of PD, an AT2R antagonist prevents NP-6AK-mediated up regulation of MCL-1, indicating that this effect is via AT2R.

AT2R activation is suppressed in a variety of disease states including hypertension, diabetes, cancers and various neurodegenerative diseases. Suppression of AT2R leads to increased activity of the AT1R which is a major contributor to metabolic diseases (e.g., cardiovascular and renal diseases, type 2 diabetes) and cancers. Therefore, the present invention provides a new class of laboratory reagents and therapeutic polypeptides which can be used to characterize and treat such disorders.

References and Definitions

The patent and scientific literature referred to herein establishes knowledge that is available to those of skill in the art. The issued U.S. patents, pending U.S. applications, published foreign patents and applications, and references, including protein and nucleotide database sequences, that are cited herein are hereby incorporated by reference to the same extent as if each was specifically and individually indicated to be incorporated by reference.

As used herein, the terms "about" or "approximately" mean within twenty percent (20%) of the numerical amount cited.

As used herein, the term "a" means one or more.

As used herein, the terms "increased" or "decreased" mean at least 10% more or less, respectively, relative to pre-treatment with an agonist of the invention.

As used herein, a "pharmaceutical composition" includes an active agent and a pharmaceutically acceptable carrier.

As used herein, the phrase "pharmaceutically acceptable" refers to molecular entities and compositions that are physiologically tolerable and do not typically produce a severe allergic, pyrogenic or similarly undesired reaction when administered to a mammal.

As used herein, the term "carrier" refers to a diluent, adjuvant, excipient, or vehicle with which a compound is administered. Such pharmaceutical carriers can be sterile liquids, such as water and oils, including those of petroleum, animal, vegetable or synthetic origin, such as peanut oil, soybean oil, mineral oil, sesame oil and the like. Water or other aqueous solutions, saline solutions, aqueous dextrose and glycerol solutions may be employed as carriers, particularly for injectable solutions. Suitable pharmaceutical carriers are described in "Remington's Pharmaceutical Sciences" by E. W. Martin (61).

Polypeptide Modulators of AT2R Activity

The invention provides a new class of agonists which are polypeptides (or polypeptide derivatives or analogues) comprising 6 amino acid residues with the generic sequence A1-A2-A3-A4-A5-A6, where A1 is Lys; A2 is Pro, 3Hyp or 4Hyp; A3 is Leu or Ile; A4 is Lys, A5 is Pro, 3Hyp or 4Hyp, and A6 is Trp (SEQ ID NO. 1). This new class is referred to as NP-6AK agonists. Sequences with Hyp in at least one position may be preferred due to increased stability. Other derivatives or analogues of these agonists may include chemical modifications that increase stability in the bloodstream for use as a pharmaceutical reagent.

One possible modification is formation of non-natural peptide bonds for additional stability or the attachment of the side chain atoms to a different atom of the residue. An example of such chemistry is cited in Hook et al. (60). The authors describe beta amino acids, wherein the side chains are attached to the beta carbon, whereas natural amino acid side chains are attached to the alpha carbon. Various studies have shown that these "beta peptides" are less likely to be degraded by non-specific peptidases compared to natural peptides. Any such chemistry that modifies the natural peptide for additional stability could be used, including peptoids in which the side chain is attached to the nitrogen.

Another method of stabilizing the polypeptides of the invention is covalent or non-covalent association with an inert water-soluble polymer. When administered systemically, therapeutic compositions are often cleared rapidly from the circulation and may therefore elicit relatively short-lived pharmacological activity. Consequently, frequent injections of relatively large doses of bioactive compounds may be required to sustain therapeutic efficacy. Any water-soluble (e.g., at least about 0.01 mg/ml) inert polymer which provides the conjugate with the desired increase in stability or half-life is suitable for use in the invention. Non-proteinaceous polymers are particularly preferred. The polymer is preferably a hydrophilic synthetic polymer, such as a polyvinyl polymer (e.g., polyvinylalcohol and polyvinylpyrrolidone), polyalkylene ether (e.g., polyethylene glycol (PEG)); polyoxyalkylene (e.g., polyoxyethylene, polyoxypropylene, and block copolymers of polyoxyethylene and polyoxypropylene (Pluronics)); polymethacrylate; or carbomer. However, natural polymers are also useful, such as branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g., polymannuronic acid, or alginic acid), D-glucosamine, D-galactosamine, D-glucose and neuraminic acid including, for example, lactose, amylopectin, starch, hydroxyethyl starch, amylose, dextran sulfate, dextran, dextrins, glycogen, or polymers of sugar alcohols such as polysorbitol and polymannitol, heparin or heparan. The molecular weight of the polymer can range from about 10,000 to 500,000 Daltons (D), and may typically be about 20,000 D, about 30,000 D, about 40,000 D, or about 50,000 D.

Compounds modified by the covalent attachment of water-soluble polymers such as polyethylene glycol (PEG), copolymers of polyethylene glycol and polypropylene glycol, or monomethoxypolyethylene glycol (mPEG), carboxymethyl cellulose, dextran, polyvinyl alcohol, polyvinylpyrrolidone or polyproline are known to exhibit substantially longer half-lives in blood following intravenous injection than do the corresponding unmodified compounds. Such modifications may also increase the composition's solubility in aqueous solution, reduce aggregation, increase the physical or chemical stability of the compound, and reduce the immunogenicity and reactivity of the composition.

Attachment of polyethylene glycol (PEG) to agonist compositions of the invention is particularly useful because PEG has very low toxicity in mammals and may reduce the immunogenicity or antigenicity of the agonist compositions. Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

The agonist compositions of the present invention may be delivered in a microencapsulation device so as to reduce or prevent a host immune response against the polypeptide or against cells which may produce the polypeptide. The polypeptide or compositions of the present invention may also be delivered microencapsulated in a membrane, such as a liposome. As an example, polymers such as PEG may be conveniently attached to one or more reactive amino acid residues in a polypeptide of the agonist compositions, such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Another method of modifying the polypeptide agonists of the invention is to add a signal sequence to the N- or C-terminus. The term "signal sequence," as used herein, refers to any short peptide that directs the trafficking of a protein in the cell. Signal sequences may, for example, direct secretion of a polypeptide, or localization within an intracellular compartment. Signal sequences also frequently determine the orientation of a peptide across a cell membrane. One example is an N-terminal sequence of about 20 amino acids that directs secretory and transmembrane proteins to the endoplasmic reticulum (ER) (see, e.g., von Heijne (1985), *J. Mol. Biol.* 184:99-105). Signal sequences may also be engineered to include one or more specific protease recognition sites, such that the signal sequences will be removed by endogenous proteases after trafficking.

AT2R Agonist Reagents

Activation of AT2R in laboratory testing is of high interest due to the many effects of AT2R described above. Therefore, in one aspect, the invention provides AT2R agonists as in vitro or in vivo reagents for laboratory research.

Thus an NP-6AK agonist to AT2R has utility as a control to characterize and quantify downstream effects of the receptor activation, such as its effects on the mammalian target of rapamycin (MTOR), NHE6, ErbB3 and Nitric Oxide Synthase.

For example, CHO cells expressing AT2R and MTOR are treated with an NP-6AK agonist and insulin to activate both MTOR and AT2R. AT2R suppresses MTOR-mediated phosphorylation of Ribosomal Protein S6 (RPS6). Western blotting can be used to determine RPS6 phosphorylation state which is decreased by at least 10% in response to AT2R activation by the agonist NP-6AK. The same cell line can then be treated with a different AT2R agonist candidate to assess the efficacy of the agonist candidate, or the same cell line can be treated with both an AT2R agonist of the invention and an AT2R antagonist candidate (e.g., EMA300, Smith et al. (2013), *Pain Medicine* 14(10):1557-68; PD123319, Chakrabarty et al. (2008), *Endocrinology* 149 (7):3452) to assess the efficacy and mode of action (i.e., competitive, non-competitive) of the antagonist candidate.

An NP-6AK agonist increases expression levels of at least one, and in some embodiments all three, MCL-1 isoforms.

Methods of Treatment

In order to treat an AT1R-mediated inflammatory response or an inflammatory response arising from underactivation of the AT2R, and/or the symptoms arising therefrom, an NP-6AK agonist is administered by any route that will permit delivery of the active agent to the affected cells. In some embodiments, administration is subcutaneous, intramuscular or intraperitoneal, but may also be by inhalation, intra-arterial, intravenous, intradermal, topical, oral, parenteral, intraventricular, or intracranial administration. Alternatively, the active agent may be delivered locally to the system or the affected cells by any suitable means.

In therapeutic treatments of the invention, a therapeutically effective amount of the pharmaceutical composition is administered to a mammalian patient. As used herein, the term "therapeutically effective amount" means an amount sufficient to reduce by at least 15 percent, preferably by at least 50 percent, more preferably by at least 90 percent, and most preferably substantially eliminate or prevent, a clinically significant metric or deficit in the activity, function and response of the patient. Specifically, a therapeutically effective amount will cause one or more of the following: decreased AT1R activation, increased AT2R activation; decreased cortisol levels; stabilized insulin levels; decreased pro-inflammatory cytokines, decreased pro-inflammatory interleukins, increased function of dopaminergic neurons, decreased Reactive Oxygen Species, decreased mucous production, or a decrease or increase in any other relevant markers as discussed herein or that would be known to one of ordinary skill in the art as it relates to cystic fibrosis (CF), diabetes, metabolic X syndrome; hyperglycemia, autism, Alzheimer's disease, inflammation or cancer. The frequency and dosage of the therapy can be titrated by the ordinary physician or veterinarian using standard dose-to-response techniques that are well known in the art.

Pharmaceutical Formulations

Liquid forms, such as lotions suitable for topical administration or for cosmetic application, may include a suitable aqueous or non-aqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like.

The above-described components for liquid, semisolid and solid topical compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

When pharmaceutical compositions are to be administered transdermally they typically are employed as liquid solutions or as gels. In these settings the concentration of agonists of the present invention range from about 0.1% to about 20%, and preferably from about 0.1% to about 10%, of the composition with the remainder being aqueous mixed or non-aqueous vehicle, such as alcohols and the like, suspending agents, gelling agents, surfactant, and the like. Examples of suitable such materials are described below.

The agonist-containing compositions of this invention can also be administered in sustained release transdermal forms or from transdermal sustained release drug delivery systems. A description of representative sustained release materials can be found in the incorporated materials in Remington's Pharmaceutical Sciences, supra.

The agonist compositions for systemic administration include compositions for oral administration, that is liquids and solids, and compositions for injection.

Compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical solvent. Typical unit dosage forms include profiled, premeasured ampules or syringes of the liquid compositions or pills, tablets, capsules or the like in the case of solid compositions. According to one embodiment, an agonist composition of the present invention is usually a minor component (from about 0.01 to about 20% by weight or preferably from about 0.1 to about 15% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature including a binder such as microcrystalline cellulose, gum tragacanth or gelatin; an solvent such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

According to another embodiment, injectable compositions are typically based upon injectable sterile saline or phosphate-buffered saline or other injectable carriers known in the art. A compound of the present invention in such compositions is typically a minor component, about 0.1-30% by weight, with the remainder being the injectable carrier and the like.

The above-described components for orally administrable or injectable compositions are merely representative. Other materials as well as processing techniques and the like are set forth in the part of Remington's Pharmaceutical Sciences noted above.

EXAMPLES

The NP-6AK agonists if the invention, including polypeptides comprising, consisting of, or consisting essentially of the sequences Lys-Pro-Leu-Lys-Pro-Trp (SEQ ID NO. 2); Lys-3Hyp-Leu-Lys-Pro-Trp (SEQ ID NO. 3); Lys-4Hyp-Leu-Lys-Pro-Trp (SEQ ID NO. 4); Lys-Pro-Ile-Lys-Pro-Trp (SEQ ID NO. 5); Lys-3Hyp-Ile-Lys-Pro-Trp (SEQ ID NO. 6); Lys-4Hyp-Ile-Lys-Pro-Trp (SEQ ID NO. 7); Lys-Pro-Leu-Lys-3Hyp-Trp (SEQ ID NO. 8); Lys-3Hyp-Leu-Lys-3Hyp-Trp (SEQ ID NO. 9); Lys-4Hyp-Leu-Lys-3Hyp-Trp (SEQ ID NO. 10); Lys-Pro-Ile-Lys-3Hyp-Trp (SEQ ID NO. 11); Lys-3Hyp-Ile-Lys-3Hyp-Trp (SEQ ID NO. 12); Lys-4Hyp-Ile-Lys-3Hyp-Trp (SEQ ID NO. 13); Lys-Pro-Leu-Lys-4Hyp-Trp (SEQ ID NO. 14); Lys-3Hyp-Leu-Lys-4Hyp-Trp (SEQ ID NO. 15); Lys-4Hyp-Leu-Lys-4Hyp-Trp (SEQ ID NO. 16); Lys-Pro-Ile-Lys-4Hyp-Trp (SEQ ID NO. 17); Lys-3Hyp-Ile-Lys-4Hyp-Trp (SEQ ID NO. 18); and Lys-4Hyp-Ile-Lys-4Hyp-Trp (SEQ ID NO. 19), can be tested in various cell-based systems to demonstrate AT2R agonist activity, and utility in the methods described herein.

Thus, an NP-6AK agonist comprising the sequence Lys-Pro-Leu-Lys-Pro-Trp (SEQ ID NO. 2) promoted cell survival across mouse HL-1 cardiomyocytes and human smooth vascular muscle cells by acting through AT2R activation. Cell survival was assessed by measurement of cell index (CI) using a Xcelligence™ Real-Time Cell Analyzer (Westburg B V, Leusden, N L) to quantitatively determine the effect of different treatments on cell survival, adhesion, and proliferation. Cell lines treated with the NP-6AK agonist (300 nM) demonstrated significantly better survival and more proliferation than those treated with CGP42112A (300 nM) (Sigma-Aldrich, Co. LLC, St. Louis, Mo.), a partial agonist of AT2R. CGP42112A and the NP-6AK agonist (300 nM) increased CI of serum starved HL-1 cells in the order CGP42112A ($\geq$14%), NP-6AK ($\geq$25%). Increase in CI is a direct effect of AT2R activation. This was verified by addition of an AT2R antagonist, PD123319 (Sigma-Aldrich, Co. LLC, St. Louis, Mo.). In the presence of this antagonist, the cell survival otherwise observed using the NP-6AK agonist was not present.

An NP-6AK agonist upregulated MCL-1 by selectively activating AT2R across several cell lines. This effect was observed in cardiomyocytes, human vascular smooth muscle cells, SH-SY5Y cells (ATCC, Manassas, Va.), and PC-12 neuronal cells (ATCC, Manassas, Va.) in conditions of serum starvation and/or toxicity. When incubated with an NP-6AK agonist at a concentration of 300 nM, cardiomyocytes displayed 45% higher MCL-1 expression and human smooth vascular muscle cells displayed 22% higher MCL-1 expression (FIG. 1). When any of these cell lines was pre-treated with an AT2R antagonist such as PD123319, the MCL-1 upregulation was not observed, implying that NP-6AK activation of AT2R is necessary for MCL-1 upregulation. Cells treated with the NP-6AK agonist generated higher MCL-1 upregulation relative to those treated with a partial agonist such as CGP42112A.

Figure 2:
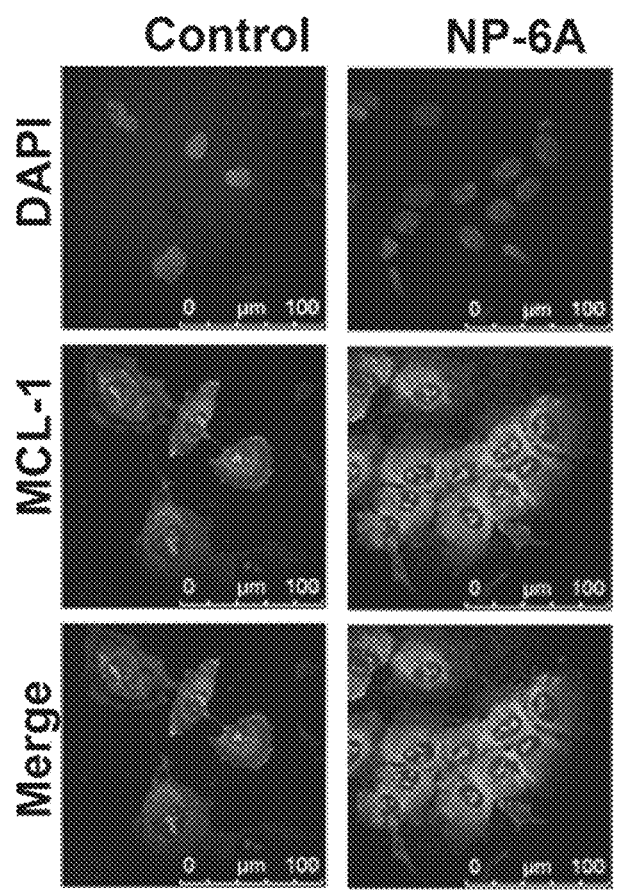
FIG. 2 shows immunofluorescence staining of SH-SY5Y cells subjected to treatments (24 hours) using an NP-6AK agonist with anti-MCL-1 antibody and nuclear stain DAPI. n≥80 and *p<0.01 compared to control. The NP-6AK agonist was more effective than the control for up regulation of MCL-1.

The SH-SY5Y cell line is a neuronal cell line with both dopaminergic and adrenergic receptors. When this cell line was treated with Rapamycin, MCL-1 expression was reduced. Addition of an NP-6AK agonist to this cell line after treatment with Rapamycin was able to recover MCL-1 expression. When just the NP-6AK agonist was added at a concentration of 300 nM, these cells displayed 2-fold increase in MCL-1 expression. See FIG. 2.

Figure 3A:
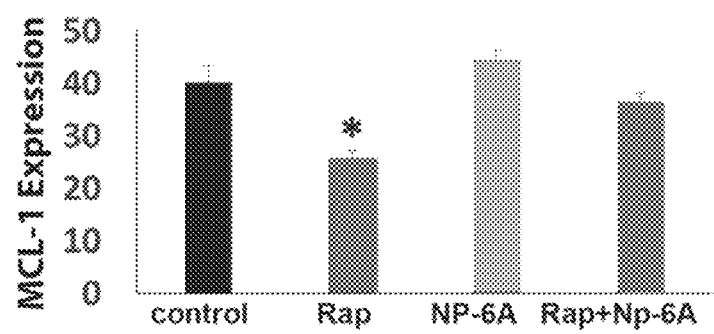
FIGS. 3A and 3B show that an NP-6AK agonist promotes neurite elongation (FIG. 3A) and reverses rapamycin-mediated suppression of MCL-1 expression (FIG. 3B) in SH-SY5Y cells.
Figure 3B:
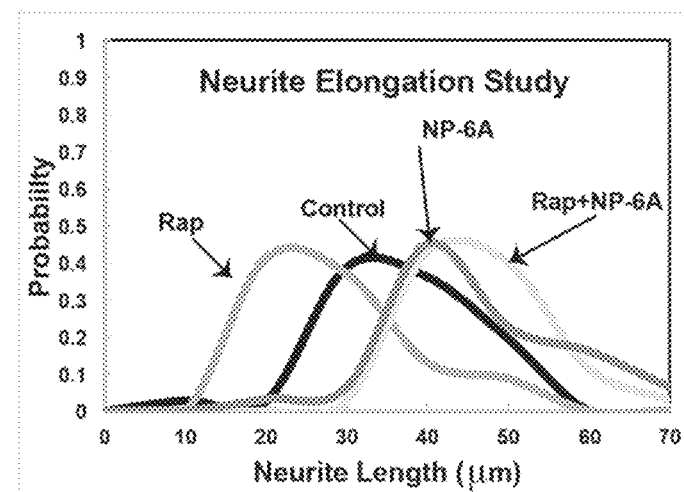

Serum-starvation reduced survival of SH-SY5Y cells and PC-12 cells. When these cell lines were treated with an NP-6AK agonist, they had a higher survival rate and demonstrated increased MCL-1 expression and neurite elongation. See FIG. 3. When PC-12 cells were treated with AT2R antagonist PD123319, the protective effects of the NP-6AK agonist were lost, indicating that the NP-6AK agonist's direct action is through AT2R activation. Treatment of this cell line with 300 nM of NP-6AK agonist led to increased cell viability by over 30% relative to treatment with native ligand of AT2R Ang II (300 nM). Relative to treatment with 300 nM CGP42112A, cells treated with an NP-6AK agonist displayed over 70% increased survival. Treatment with AngII or CGP42112A was more detrimental relative to results obtained when cells are treated with AT2R antagonist PD123319. AT2R activation by NP-6AK agonist promotes cell survival whereas AT2R activation by other ligands are harmful to it. These results were assessed using an MTS cell proliferation assay (Biovision Inc., Milpitas, Calif.).

Figure 4:
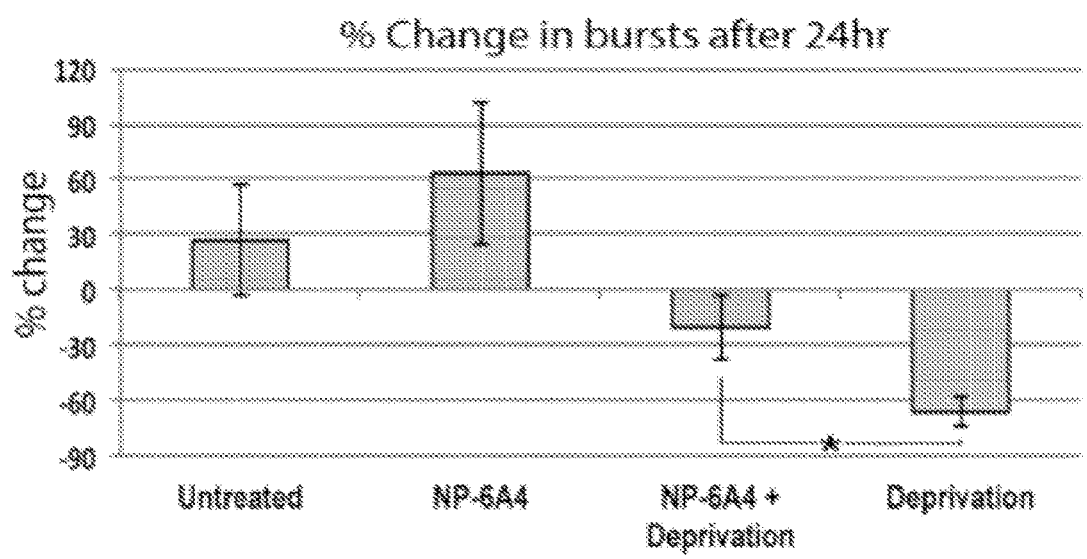
FIG. 4 shows data from studies with ex vivo tissue that demonstrated that an NP-6AK agonist provided neuroprotection to normal primary murine embryonic cortical neurons in culture when challenged with nutrient deprivation. For nutrient deprivation, primary cortical neurons (14 DIV) were incubated in glucose-free Locke's medium with or without 300 nm NP-6AK agonist. Cells treated with an NP-6AK agonist had a 60% increased activity (p<0.05) compared with negative controls, corroborating previous data showing increased cell viability under conditions of serum starvation and neuroprotection.

Ex vivo neurons were obtained and treated with an NP-6AK agonist in different conditions to assess neuroprotective properties. Normal primary murine embryonic cortical neurons in culture (14 days in vitro) were challenged with nutrient deprivation by incubation in glucose-free Locke's medium (Schnapf et al. (1990)). These cultures were then supplemented with 300 nM NP-6AK agonist or no NP-6AK agonist. Cultures that were supplemented 300 nm NP-6AK agonist demonstrated 60% increased activity ($p<0.05$) compared with negative controls. See FIG. 4.

Zucker Obese (ZO) rats (Charles River Laboratories, Inc., Wilmington, Mass.), a diabetic animal model displaying signs of cardiovascular disease were treated for 2 weeks (dose of 0.9 mg/kg/day) via subcutaneous injection with an NP-6AK agonist and assessed for several markers of cardiovascular health including blood markers and structural parameters of the heart. Controls were ZO rats that received saline. Fasting plasma and urine profiles demonstrated that animals receiving the NP-6AK agonist had reduced triglycerides (~50%), urine protein (~68%), reduced urine N-acetyl-beta-A-glucosaminidase (~60%), and increased HDL by 12% on average. Echocardiography performed using the Vevo® 2100 platform (VisualSonics, Toronto, Ontario, CA) indicated that animals treated with the NP-6AK agonist had improved structural cardiac parameters including circumferential strain of endocardium (short axis view), and myocardial performance index (MPI) ($p\leq0.005$), and E/E' ratio ($p\leq0.002$), a powerful predictor of primary cardiac events. See Table 1.

TABLE 1

| Treatment groups (2 Weeks; Saline or NP-6A 0.9 mg/kg/day) | Plasma Profile mg/dL | | Urine Profile mg/dL | | Echocardiography/Strain analysis | | |
|---|---|---|---|---|---|---|---|
| | Triglycerides | HDL | Protein | NA6 | MPI | E/E | Circumferential Strain |
| Male ZO rat ± Saline | 1229 ± 164 | 65 ± 4.1 | 1426.7 ± 649.5 | 27.9 ± 6.4 | 0.516 ± 0.03 | 32.3 ± 2.06 | −20.56 ± 1.65 |
| Male ZO rat ± NP-6A | 610 ± 109 | 73 ± 2.8 | 445 ± 86.4 | 10.9 ± 1.5 | 0.389 ± 0.02 | 26 ± 2.1 | −26.11 ± 2.47 |

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited herein are hereby incorporated by reference.

REFERENCES

1. Kalupahana and Moustaid-Moussa (2012), "The renin-angiotensin system: a link between obesity, inflammation and insulin resistance," *Obes. Rev.* 13(2):136-49.
2. Santos et al. (2014), "The Therapeutic Role of Renin-Angiotensin System Blockers in Obesity-Related Renal Disorders," *Curr. Clin. Pharmacol.* 9(1):2-9.
3. Saavedra et al. (2011), "Blockade of brain angiotensin II AT1 receptors ameliorates stress, anxiety, brain inflammation and ischemia: Therapeutic implications," *Psychoneuroendocrinology* 36(1):1-18.
4. Herr et al. (2008), "Potential role of Renin-Angiotensin-system for tumor angiogenesis in receptor negative breast cancer," *Gynecol. Oncol.* 109:418-25.
5. Kintscher et al. (2009), "Inhibiting angiotensin type 1 receptors as a target for diabetes," *Expert Opin. Ther. Targets* 10:1257-63.
6. Vinson et al. (2012), "The renin-angiotensin system in the breast and breast cancer," *Endocr. Relat. Cancer* 19(1):R1-19.
7. Steckelings et al. (2012), "AT2 receptor agonists: hypertension and beyond," *Curr. Opin. Nephrol. Hypertens.* 21(2):142-6.
8. McCarthy et al. (2009), "Angiotensin AT2 receptor stimulation causes neuroprotection in a conscious rat model of stroke," *Stroke* 40:1482-9.
9. Ferreira et al. (2010), "Therapeutic implications of the vasoprotective axis of the renin-angiotensin system in cardiovascular diseases," *Hypertension* 55(2):207-13.
10. Doi et al. (2010), "Angiotensin II type 2 receptor signaling significantly attenuates growth of murine pancreatic carcinoma grafts in syngeneic mice," *BMC Cancer* 10:67.
11. Pickel et al. (2010), "Overexpression of angiotensin II type 2 receptor gene induces cell death in lung adenocarcinoma cells," *Cancer Biol. Ther.* 9(4):277-85.
12. Brown et al. (2006), "AT2 receptor stimulation may halt progression of pheochromocytoma," *Ann. N.Y. Acad. Sci.* 1073:436-43.
13. Adachi et al. (2003), "Angiotensin II type 2 receptor deficiency exacerbates heart failure and reduces survival after acute myocardial infarction in mice," *Circulation.* 107:2406-8.
14. Ohinata et al. (2009), "Orally administered novokinin, an angiotensin AT2 receptor agonist, suppresses food intake via prostaglandin E2-dependent mechanism in mice," *Peptides* 30:1105-8.
15. Unger and Dahlöf (2010), "Compound 21, the first orally active, selective agonist of the angiotensin II type 2 (AT2) receptor: implications for AT2 receptor research and therapeutic potential," *J. Renin Angiotensin Aldosterone Syst.* 11:75-7.
16. Qi et al. (2012), "Moderate cardiac-selective overexpression of angiotensin II type 2 receptor protects cardiac functions from ischaemic injury," *Exp. Physiol.* 97:89-101.
17. Oishi et al. (2006), "AT2 receptor mediates the cardioprotective effects of AT1 receptor antagonist in post-myocardial infarction remodeling," *Life Sci.* 80(1):82-8.
18. Carey et al. (2000), "Role of the Angiotensin Type 2 Receptor in the Regulation of Blood Pressure and Renal Function," *Hypertension* 35(1):155-163.
19. Ohinata et al. (2009), "Orally administered novokinin, an angiotensin AT2 receptor agonist, suppresses food intake via prostaglandin E2-dependent mechanism in mice," *Peptides* 30:1105-1108.
20. Guimond and Gallo-Payet (2012), "How does angiotensin AT(2) receptor activation help neuronal differentiation and improve neuronal pathological situations?" *Front Endocrinol. (Lausanne)* 3:164.
21. Siragy and Carey (1997), "The subtype 2 (AT2) angiotensin receptor mediates renal production of nitric oxide in conscious rats," *J. Clin. Invest.* 100:264-269.
22. Widdop et al. (2002), "AT2 receptor-mediated relaxation is preserved after long-term AT1 receptor blockade," *Hypertension* 40:516-520.

23. Yayama et al. (2006), "Angiotensin II stimulates endothelial NO synthase phosphorylation in thoracic aorta of mice with abdominal aortic banding via type-2 receptor," *Hypertension* 48:958-964.
24. Rodrigues-Ferreira and Nahmias (2010), "An atypical family of angiotensin II AT2 receptor-interacting proteins," *Trends Endocrinol. Metab.* 21:684-690.
25. Knowle et al. (2000), "Identification of an interaction between the angiotensin II receptor sub-type AT2 and the ErbB3 receptor, a member of the epidermal growth factor receptor family," *Regul. Pept.* 87(1-3):73-82.
26. Pulakat et al. (2005), "Ligand-dependent complex formation between the Angiotensin II receptor subtype AT2 and Na+/H+ exchanger NHE6 in mammalian cells," *Peptides* 26(5):863-73.
27. Yamada et al. (1996), "Angiotensin II type 2 receptor mediates programmed cell death," *Proc. Natl. Acad. Sci.* (USA) 93(1):156-60.
28. Lehtonen et al. (1999), "Analysis of functional domains of angiotensin II type 2 receptor involved in apoptosis," *Mol. Endocrinol.* 13(7):1051-60.
29. Pulakat et al. (2005), "Roles of the intracellular regions of angiotensin II receptor AT2 in mediating reduction of intracellular cGMP levels," *Cell Signal.* 17(3):395-404.
30. Pulakat et al. (2002), "Role of C-terminal cytoplasmic domain of the AT2 receptor in ligand binding and signaling," *FEBS Lett.* 524(1-3):73-8.
31. Gendron et al. (2003), "The angiotensin type 2 receptor of angiotensin II and neuronal differentiation: from observations to mechanisms," *J. Mol. Endocrinol.* 31(3):359-72.
32. Rodriguez-Pallares et al. (2004), "Angiotensin II increases differentiation of dopaminergic neurons from mesencephalic precursors via angiotensin type 2 receptors," *Eur. J. Neurosci.* 20(6):1489-98.
33. Zawada et al. (2005), "Angiotensin II protects cultured midbrain dopaminergic neurons against rotenone-induced cell death," *Brain Res.* 1045(1-2):64-71.
34. Mendelsohn et al. (1988), "Localization of angiotensin II receptor binding in rabbit brain by in vitro autoradiography," *J. Comp. Neurol.* 270:372-384.
35. Unger et al. (1988), "Brain angiotensin: pathways and pharmacology," *Circulation* 77(60):I40-54.
36. Severs and Daniels-Severs (1973), "Effects of angiotensin on the central nervous system," *Pharmacol. Rev.* 25:415-449.
37. Phillips (1987), "Functions of angiotensin in the central nervous system," *Ann. Rev. Physiol.* 49:413-435.
38. Nuyt et al. (1999), "Ontogeny of angiotensin II type 2 receptor mRNA expression in fetal and neonatal rat brain," *J. Comp. Neurol.* 407:193-206
39. Song et al. (1992), "Mapping of angiotensin II receptor subtype heterogeneity in rat brain," *J. Comp. Neurol.* 316:467-484.
40. Lenkei et al. (1996), "Distribution of angiotensin II type-2 receptor (AT2) mRNA expression in the adult rat brain," *J. Comp. Neurol.* 373:322-339.
41. Lenkei et al. (1997), "Expression of angiotensin type-1 (AT1) and type-2 (AT2) receptor mRNAs in the adult rat brain: a functional neuroanatomical review," *Front. Neuroendocrinol.* 18:383-439.
42. Bottari et al. (1992), "Characterization and distribution of angiotensin II binding sites in fetal and neonatal astrocytes from different rat brain regions," *Brain Res.* 585:372-376.A.
43. Okamura et al. (1999), "Upregulation of renin-angiotensin system during differentiation of monocytes to macrophages," *J. Hypertens.* 17(4):537-545.
44. Nahmod et al. (2003), "Control of dendritic cell differentiation by angiotensin II," *FASEB J.* 17(3):491-493.
45. Iwanami et al. (2011), "Effect of angiotensin II type 2 receptor deletion in hematopoietic cells on brain ischemia-reperfusion injury," *Hypertension* 58(3):404-409.
46. Borlongan et al. (2011), "The great migration of bone marrow-derived stem cells toward the ischemic brain: therapeutic implications for stroke and other neurological disorders," *Prog. Neurobiol.* 95(2):213-228.
47. Padia et al. (2012), "Mechanisms of dopamine D(1) and angiotensin type 2 receptor interaction in natriuresis," *Hypertension* 59(2):437-45.
48. Namsolleck et al. (2013), "AT2-receptor stimulation enhances axonal plasticity after spinal cord injury by upregulating BDNF expression," *Neurobiol Dis.* 51:177-91.
49. Guimond et al. (2013), "Expression and role of the angiotensin II AT2 receptor in human prostate tissue: in search of a new therapeutic option for prostate cancer." *The Prostate* 73(10):1057-1068.
50. Wruck et al. (2005), "Regulation of transport of the angiotensin AT2 receptor by a novel membrane-associated Golgi protein,"*Arterioscler. Thromb. Vasc. Biol.* 25(1):57-64.
51. Libby et al. (2002), "Inflammation and Atherosclerosis," *Circulation* 105(9):1135-1143.
52. LaMarca (2011), "Hypertension in Response to IL-6 During Pregnancy: Role of AT1-receptor Activation." *Int. J. Interferon Cytokine Mediator Res.* 2011(3):65-70.
53. Mitra et al. (2010), "Angiotensin II-induced Upregulation of AT1-receptor Expression: Sequential Activation of NFkB and Elk-1 in Neurons."*Am. J. Physiol. Cell Physiol.* 299(3):C561-9.
54. Mizushima et al. (2010), "Blockage of Angiotensin II Type 1 Receptor Regulates TNF-α-induced MAdCAM-1 Expression via Inhibition of NF-κB Translocation to the Nucleus and Ameliorates Colitis."*Am. J. Physiol. Gastrointest. Liver Physiol.* 298(2): G255-G266.
55. Dronavalli et al. (2008), "The pathogenesis of diabetic nephropathy." *Nat. Clin. Pract. Endocrinol. Metab.* 4(8): 444-452.
56. Parving et al. (2012), "Cardiorenal End Points in a Trial of Aliskiren for Type 2 Diabetes." *New Eng. J. Med.* 367(23):2204-2213.
57. Harel et al. (2012), "The Effect of Combination Treatment with Aliskiren and Blockers of the Renin-angiotensin System on Hyperkalaemia and Acute Kidney Injury: Systematic Review and Meta-analysis." *BMJ* 344 (1):e42-e42.
58. Liebson and Amsterdam (2009), "Ongoing Telmisartan Alone and in Combination With Ramipril Global Endpoint Trial (ONTARGET): Implications for Reduced Cardiovascular Risk." *Prev. Cardiol.* 12(1):43-50.
59. Unger (2003), "The Ongoing Telmisartan Alone and in Combination with Ramipril Global Endpoint Trial Program," *Am. J. Cardiol.* 91(10A):28G-34G.
60. Hook et al. (2005), "The Proteolytic Stability of 'Designed' Beta-peptides Containing Alpha-peptide-bond Mimics and of Mixed Alpha,beta-peptides: Application to the Construction of MHC-binding Peptides," *Chem. Biodivers.* 2(5):591-632.
61. Remington's Pharmaceutical Sciences (18th Ed., E. W. Martin (ed.), Mack Publishing Co., Easton, Pa.

62. Abadir et al. (2011), "Identification and Characterization of a Functional Mitochondrial Angiotensin System," *Proc. Natl. Acad. Sci.* (USA) 108(36):14849-14854.
63. Thathiah and De Strooper (2011), "The Role of G Protein-coupled Receptors in the Pathology of Alzheimer's Disease," *Nat. Rev. Neurosci.* 12(2):73-87.
64. Abdalla et al. (2009), "Angiotensin II AT2 Receptor Oligomers Mediate G-protein Dysfunction in an Animal Model of Alzheimer Disease," *J. Biol. Chem.* 284(10): 6554-6565.
65. Kurihara et al. (2006), "Neuroprotective Effects of Angiotensin II Type 1 Receptor (AT1R) Blocker, Telmisartan, via Modulating AT1R and AT2R Signaling in Retinal Inflammation," *Invest. Ophthalmol. Vis. Sci.* 47(12):5545-5552.
66. Benigni et al. (2009), "Disruption of the Ang II Type 1 Receptor Promotes Longevity in Mice," *J. Clin. Invest.* 119(3):524-530.
67. Weir et al. (2012), "CNS SIRT3 Expression Is Altered by Reactive Oxygen Species and in Alzheimer's Disease," *PLoS ONE* 7(11):e48225.
68. Deane et al. (2013), "Enhanced recruitment of endosomal Na+/H+ exchanger NHE6 into Dendritic spines of hippocampal pyramidal neurons during NMDA receptor-dependent long-term potentiation." *J. Neurosci.* 33(2): 595-610.
69. Schwede et al. (2013), "Genes for Endosomal NHE6 and NHE9 Are Misregulated in Autism Brains," *Mol. Psychiatry* 19(3):277-9.
70. Xinhan et al. (2011), "Na+/H+ Exchanger Isoform 6 (NHE6/SLC9A6) Is Involved in Clathrin-dependent Endocytosis of Transferrin," *Am. J. Physiol. Cell Physiol.* 301(6):C1431-C1444.
71. Kumar et al. (2002), "Identification of the Region of AT2 Receptor Needed for Inhibition of the AT1 Receptor-mediated Inositol 1,4,5-triphosphate Generation." *FEBS Lett.* 532(3):379-86.
72. Hetrick et al. (2008), "Ligand mediated protein-protein interaction between the angiotensin receptor type AT1 and the human NHE6 isoform." *FASEB J.* 22:726.5.
73. Gul et al. (2012), "RAS-Mediated Adaptive Mechanisms in Cardiovascular Tissues: Confounding Factors of RAS Blockade Therapy and Alternative Approaches," *Cardiorenal Med.* 2(4):268-280.
74. Shieh et al. (2009), "Modification of alternative splicing of Mcl-1 pre-mRNA using antisense morpholino oligonucleotides induces apoptosis in basal cell carcinoma cells," *J. Invest. Dermatol.* 129(10):2497-506.
75. Bae et al. (2000), "MCL-1S, a splicing variant of the antiapoptotic BCL-2 family member MCL-1, encodes a proapoptotic protein possessing only the BH3 domain," *J. Biol. Chem.* 275(33):25255-61.
76. Yang et al. (1996), "MCL-1, a member of the BLC-2 family, is induced rapidly in response to signals for cell differentiation or death, but not to signals for cell proliferation," *J. Cell Physiol.* 166(3):523-36.
77. Thomas et al. (2010), "Mcl-1: the molecular regulation of protein function," *FEBS Lett.* 584(14):2981-9.

What is claimed:

1. A pharmaceutical composition comprising a polypeptide comprising the amino acid sequence that corresponds to the formula SEQ ID NO: 1

A1-A2-A3-A4-A5-A6 wherein:
A1 is Lys;
A2 is Pro, 3Hyp or 4Hyp;
A3 is Leu or Ile;
A4 is Lys;
A5 is Pro, 3Hyp or 4Hyp; and
A6 is Trp.

2. A pharmaceutical composition comprising a polypeptide consisting essentially of the amino acid sequence that corresponds to the formula SEQ ID NO: 1

A1-A2-A3-A4-A5-A6 wherein:
A1 is Lys;
A2 is Pro, 3Hyp or 4Hyp;
A3 is Leu or Ile;
A4 is Lys;
A5 is Pro, 3Hyp or 4Hyp; and
A6 is Trp.

3. A pharmaceutical composition comprising a polypeptide consisting of the amino acid sequence that corresponds to the formula SEQ ID NO: 1

A1-A2-A3-A4-A5-A6 wherein:
A1 is Lys;
A2 is Pro, 3Hyp or 4Hyp;
A3 is Leu or Ile;
A4 is Lys;
A5 is Pro, 3Hyp or 4Hyp; and
A6 is Trp.

4. The pharmaceutical composition of claim 1 wherein the polypeptide has Angiotensin II Type 2 Receptor (AT2R) agonist activity when administered to a cell expressing an AT2R receptor.

5. The pharmaceutical composition of claim 1 wherein:
when A2 is Pro, A5 is 3Hyp or 4Hyp; or
when A5 is Pro, A2 is 3Hyp or 4Hyp.

6. The pharmaceutical composition of claim 1 wherein the composition is lyophilized.

7. The pharmaceutical composition of claim 1 further comprising a pharmaceutically acceptable carrier.

* * * * *

```
                        SEQUENCE LISTING

<160> NUMBER OF SEQ ID NOS: 21

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pro, 3Hyp or 4Hyp
<220> FEATURE:
<221> NAME/KEY: MOD_RES
<222> LOCATION: (3)..(3)
<223> OTHER INFORMATION: Leu or Ile
<220> FEATURE:
<221> NAME/KEY: MOD_RES
<222> LOCATION: (5)..(5)
<223> OTHER INFORMATION: Pro, 3Hyp or 4Hyp

<400> SEQUENCE: 1

Lys Xaa Xaa Lys Xaa Trp
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Pro Leu Lys Pro Trp
1               5
```

```
<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 3Hyp

<400> SEQUENCE: 3

Lys Xaa Leu Lys Pro Trp
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 4Hyp

<400> SEQUENCE: 4

Lys Xaa Leu Lys Pro Trp
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Pro Ile Lys Pro Trp
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 3Hyp

<400> SEQUENCE: 6

Lys Xaa Ile Lys Pro Trp
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

```
<223> OTHER INFORMATION: 4Hyp

<400> SEQUENCE: 7

Lys Xaa Ile Lys Pro Trp
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 3Hyp

<400> SEQUENCE: 8

Lys Pro Leu Lys Xaa Trp
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 3Hyp
<220> FEATURE:
<221> NAME/KEY: MOD_RES
<222> LOCATION: (5)..(5)
<223> OTHER INFORMATION: 3Hyp

<400> SEQUENCE: 9

Lys Xaa Leu Lys Xaa Trp
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 3Hyp

<400> SEQUENCE: 10

Lys Xaa Leu Lys Xaa Trp
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (5)..(5)
<223> OTHER INFORMATION: 3Hyp

<400> SEQUENCE: 11

Lys Pro Ile Lys Xaa Trp
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 3Hyp
<220> FEATURE:
<221> NAME/KEY: MOD_RES
<222> LOCATION: (5)..(5)
<223> OTHER INFORMATION: 3Hyp

<400> SEQUENCE: 12

Lys Xaa Ile Lys Xaa Trp
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 3Hyp

<400> SEQUENCE: 13

Lys Xaa Ile Lys Xaa Trp
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4Hyp

<400> SEQUENCE: 14

Lys Pro Leu Lys Xaa Trp
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: 3Hyp
<220> FEATURE:
<221> NAME/KEY: MOD_RES
<222> LOCATION: (5)..(5)
<223> OTHER INFORMATION: 4Hyp

<400> SEQUENCE: 15

Lys Xaa Leu Lys Xaa Trp
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp

<400> SEQUENCE: 16

Lys Xaa Leu Lys Xaa Trp
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4Hyp

<400> SEQUENCE: 17

Lys Pro Ile Lys Xaa Trp
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 3Hyp
<220> FEATURE:
<221> NAME/KEY: MOD_RES
<222> LOCATION: (5)..(5)
<223> OTHER INFORMATION: 4Hyp

<400> SEQUENCE: 18

Lys Xaa Ile Lys Xaa Trp
1               5

<210> SEQ ID NO 19
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 4Hyp
<220> FEATURE:
<221> NAME/KEY: MOD_RES
<222> LOCATION: (5)..(5)
<223> OTHER INFORMATION: 4Hyp

<400> SEQUENCE: 19

Lys Xaa Ile Lys Xaa Trp
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Leu or Ile
<220> FEATURE:
<221> NAME/KEY: MOD_RES
<222> LOCATION: (5)..(5)
<223> OTHER INFORMATION: 3Hyp or 4Hyp

<400> SEQUENCE: 20

Lys Pro Xaa Lys Xaa Trp
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 3Hyp or 4Hyp
<220> FEATURE:
<221> NAME/KEY: MOD_RES
<222> LOCATION: (3)..(3)
<223> OTHER INFORMATION: Leu or Ile

<400> SEQUENCE: 21

Lys Xaa Xaa Lys Pro Trp
1               5
```